US005951987A

United States Patent [19]

Cherwonogrodzky et al.

[11] Patent Number: 5,951,987

[45] **Date of Patent: *Sep. 14, 1999**

[54] POLYSACCHARIDE VACCINE TO ENHANCE IMMUNITY AGAINST BRUCELLOSIS

[75] Inventors: John W. Cherwonogrodzky; Jonathan P. Wong, both of Medicine Hat; Vincent L. Di Ninno, Redcliff, all of Canada

[73] Assignee: Her Majesty the Queen as represented by the Minister of National Defence of Her Majesty'Canadian Government, Ontario, Canada

[ * ] Notice: This patent issued on a continued prosecution application filed under 37 CFR 1.53(d), and is subject to the twenty year patent term provisions of 35 U.S.C. 154(a)(2).

[21] Appl. No.: 08/672,063

[22] Filed: Sep. 16, 1996

[30] Foreign Application Priority Data

Nov. 30, 1995 [CA] Canada .................................. 2164155

[51] Int. Cl.[6] .......................... A61K 39/10; A61K 39/02

[52] U.S. Cl. .................................... 424/252.1; 424/184.1; 424/197.11; 424/234.1; 424/235.1; 424/241.1; 424/249.1; 424/255.1; 424/256.1; 424/257.1; 424/258.1; 424/260.1; 424/261.1; 514/54; 536/123; 536/123.1; 536/127; 536/1.11

[58] Field of Search ........................... 424/184.1, 197.11, 424/252.1, 234.1, 235.1, 241.1, 249.1, 255.1, 256.1, 257.1, 258.1, 260.1, 261.1; 514/54; 536/123, 123.1, 127, 1.11

[56] References Cited

U.S. PATENT DOCUMENTS

| | | |
|---|---|---|
| 4,707,543 | 11/1987 | Zollinger et al. . |
| 4,831,126 | 5/1989 | Bundle et al. . |
| 5,006,463 | 4/1991 | Cherwonogrodzky et al. . |
| 5,225,194 | 7/1993 | Suer . |

FOREIGN PATENT DOCUMENTS

| | | |
|---|---|---|
| 1212051 | 9/1986 | Canada . |
| 8900860 | 9/1989 | WIPO . |
| 9316728 | 2/1993 | WIPO . |

OTHER PUBLICATIONS

"Antigens of Brucella" by J. Cherwonogrodzky et al, pp. 19–64, In: K. Nielsen, J.R. Duncan (ed.) 1990 Animal Brucellosis CRC Press, Boca Raton mentioned on p. 4 of the application.

"Sensitive fluorogenic enzyme immunoassay on nitrocellulose membranes for quantitation of virus" by Roberta E. Fulton et al, Jrn. of Virological Methods, 22 (1988) pp. 149 to 164 (mentioned on p. 7 of the application).

"Laboratory Animal Models for Brucellosis Studies" by Casimiro Garcia–Carrillo pp. 423 to 442, In: K Nielsen, J.R. Duncan (ed) 1990 Animal Brucellosis (mentioned on p. 9 of the application).

"The Pathogenesis and Pathobiology of Brucella Infection in Domestic Animals" by Fred M. Enright, pp. 301 to 320, In: K. Nielsen, J.R. Duncan (ed.) 1990 Animal Brucellosis (mentioned on p. 14 of the application).

"Radial Immunodiffusion Test with a Brucella Polysaccharide Antigen for Differentiating Infected from Vaccinated Cattle" by Ramon Diaz et al, pp. 37 to 41 in Jrn. of Clinical Microbiology, Jul. 1979 (mentioned on p. 14 of the application).

P. Nicoletti et al. "The Immune response to *B. Abortus:* . . . " Animal Brucellosis, Chapter 4, pp. 83–95, 1990.

L. Corbeil et al. "Killing of *Brucella abortus* by bovine serum" Infection and Immunity, Dec. 1988, vol. 56, No. 12, pp. 3251–3261.

Wong et al (1992) Immunology. vol. 77, 123–128.

Stevens et al (1995) Infect. & Immunity. vol. 63(1), 264–270.

*Primary Examiner*—Anthony C. Caputa
*Assistant Examiner*—Khalid Masood
*Attorney, Agent, or Firm*—Nixon & Vanderhye, P.C.

[57] ABSTRACT

A vaccine comprising purified outer-polysaccharide (OPS) is effective for protection against brucellosis. The vaccine is derived from Brucella or a variety of cross reactive bacteria. The vaccine can be administered by different routes (intramuscularly, subcutaneously, intraperitoneally, orally). The vaccine is effective in protecting against other infectious bacteria, aside from Brucella. It is likely that the vaccine can be given after infection to reduce illness.

13 Claims, 8 Drawing Sheets

POLYSACCHARIDE VACCINE TO ENHANCE IMMUNITY AGAINST BRUCELLOSIS

BACKGROUND OF THE INVENTION

Brucellosis is a debilitating disease that can cause abortions and weight loss in animals, "undulating" fevers, "night sweats", incapacitation and arthritis in humans. It is very hardy to environmental factors, easily aerosolized and infectious through skin abrasions, ingestion and the pulmonary route. It is difficult to treat with antibiotics and often persists as a life-long infection. Brucellosis is a disease endemic to most countries, especially under-developed nations where it infects 0.1 to 10% of the livestock (e.g. cattle, swine, sheep, goats, dogs and poultry), wild life (e.g. bison, caribou, wolves, dolphins) and people.

Currently, there are no vaccines for human use to protect against brucellosis. In the past researchers have vaccinated people at high risk (e.g. veterinarians, abattoir workers) with an attenuated vaccine strain, *B. abortus* S19, but this appears to be attenuated for cattle and can be pathogenic or cause brucellosis in humans. There was a French vaccine (PI, or phenol insoluble) that removed the toxic lipopolysaccharide (LPS) component with phenol, but the phenol insoluble residue gave a high rate of reactogenicity (at least 53%) and led to hyper-sensitivity (vaccinates exposed to Brucella antigens were susceptible to anaphylactic shock). This latter vaccine has been discontinued and hence there are no human vaccines for brucellosis presently available.

The vaccines presently used for livestock also have their inadequacies. The one used for cattle, an attenuated *B. abortus* S19 vaccine strain, does not give absolute protection from disease and is about 80% protective, occasionally reverts to a pathogenic form that can cause abortions, the vaccinates cause confusion in serological tests (i.e. in some cases the positive serology can be caused by vaccination, infection, or vaccination and subsequent infection), it is virulent for animals other than cattle and it can be pathogenic for people.

In the development of a vaccine against brucellosis, the view of the scientific community was exceptionally discouraging. Below are the key points they raised:

1) Brucella was recognized over 100 years ago and for over a century researchers around the world have tried to raise a vaccine against brucellosis without success. Given the time, number of investigators and talent involved, the evidence was obvious that a vaccine could not be developed.

2) Brucella was a facultative parasite that could sequester inside tissues. Not only was it protected from antibiotics and vaccine-induced antibodies of humoral immunity, but it also had mechanisms for controlling its host phagocyte (i.e. it secretes thymidine and cyclic GMP which inactivate the host cell) and hence cellular immunity is ineffective.

3) Polysaccharides and bacterial glucans are very poor immunogens. The evidence is that these are the least likely candidates for vaccines.

SUMMARY OF THE INVENTION

Accordingly, it is an object of the present invention to provide a safe and effective vaccine against brucellosis.

Specifically, the invention provides a vaccine, for stimulating protection against brucellosis, comprising as the active component an immunoprotective and non-toxic quantity of outer-polysaccharide (OPS) extracted from *Brucella abortus* or any bacteria cross reactive thereto.

Further, the vaccine can be used for protection against infection from a variety of bacteria.

In addition, the vaccine can be used as a brucellosis treatment after infection.

BRIEF DESCRIPTION OF THE DRAWINGS

These and other features of the invention will become more apparent in the following detailed description in which reference is made to the appended drawings wherein.

DETAILED DESCRIPTION OF THE PREFERRED EMBODIMENTS

Figure 1B:
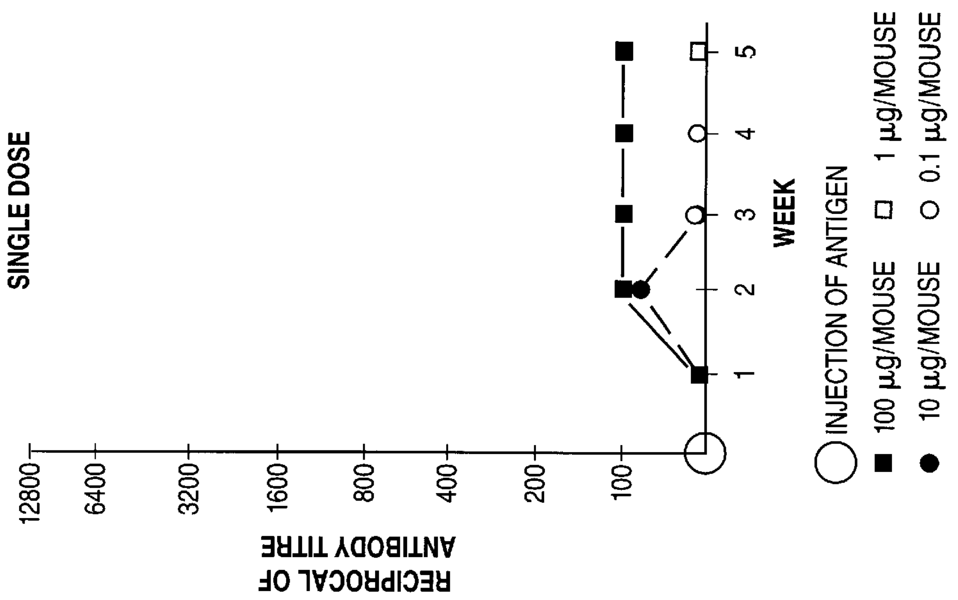
FIGS. 1 to 8 illustrate the humoral response to *Brucella abortus* antigen in mice tests.

Despite the views of world renowned Brucella experts and polysaccharide chemists, there were a few observations that gave indications that a vaccine was possible:

1) Protection does occur in the field. Brucella is only about 70% infectious (either to animals or people) which suggests that there is something occurring to protect the 30% which do not come down with brucellosis. Also, once a cow aborts due to Brucella, it has a natural immunity to this disease.

2) There was an unexplained but well accepted observation: although the outer polysaccharide (O-polysaccharide or OPS), which gives a bacterium its serological identity, does not induce an immunological response, the immunodominant antigen of Brucella (about 80% of the antibodies are to this) is this same OPS when it forms part of the bacterial LPS or smooth lipopolysaccharide.

3) It has been determined that Brucella infected animals did produce antibodies which could precipitate OPS only when it was part of LPS (Bundle et al., Canadian Patent No. 1,212,051, issued Sep. 30, 1986). It was evident that the OPS was somehow involved with immunity but that this immunity was different from antibody activity. As investigators have never reported the use of OPS as a vaccine, there appeared to be an exceptional opportunity ignored by everyone else.

4) Further, OPS was on hand for vaccine trials due to new methods in its purification (Cherwonogrodzky et al., "Antigens of Brucella", *Animal Brucellosis* (1990), 19–64, K. Nielsen and J. R. Duncan (ed.)).

The other concept advanced by the present inventors was the ability of one vaccine to protect against other cross-reactive diseases. Table I shows that several bacteria have similar OPS structures. As will be noted later, proof for this claim is the finding that the *B. abortus* OPS is a very effective vaccine for protecting pigs from *B. suis* infections. Also, the *Yersinia enterocolitica* 0:9 OPS can replace the OPS of *B. abortus* in general immunity experiments in mice.

Therefore, the present study examined the use of OPS as a vaccine to protect Balb/c mice from brucellosis.

MATERIALS AND METHODS

*Brucella abortus* 30, 413 and 2308 were acquired from Agriculture Canada, Animal Diseases Research Institute (ADRI-Nepean), Nepean, Ontario, Canada. The bacteria were grown either in Brucella broth (Difco/BDH Inc., Edmonton, Alberta) or on Brucella agar plates (supplemented with I ppm crystal violet) and incubated with 5% $CO_2$ at 37° C. for 2 days. To make an inoculum for mice, it was observed that a suspension of *B. abortus* that gave an $OD_{620}$ of 0.2 on a Spectronic 20™ spectrophotometer (Milton Roy Co., Fisher Scientific Co., Ottawa, Ontario) corresponded to $1.1\times10^9$ colony forming units (cfu). Bacterial cultures were either diluted or suspended in sterile 1% saline to approximate this value, diluted further to yield about $2.5\times10^5$ cfu/ml (0.2 ml of this suspension was the inoculum) then part of this was placed on Brucella agar and incubated to confirm these estimates.

The OPS and LPS used as vaccines were purified by methods already reported (Cherwonogrodzky et al., 1990) from *B. abortus* 413 cells killed with 2% phenol. Briefly, for OPS, the killed cells were suspended in 2% acetic acid, 1% saline solution (the suspension was 20% cells, v/v), placed in a boiling water bath for 2 hours, centrifuged to remove the cells, trichloroacetic acid (final concentration 0.2M) was added to remove proteins, centrifuged and the supernatant was extracted at room temperature with an equal volume of phenol. The OPS was precipitated from the phenol layer with 3 washes of 5 volumes of methanol with 1% sodium acetate (w/v), dialysed then purified on a G-50 Sephadex™ with 0.4% acetic acid and 0.4% pyridine as the buffer, then lyophilized. For LPS, the killed cells were suspended in 1% saline (cells were 20% v/v) and extracted with an equal volume of phenol, the mixture being constantly stirred at 70° C. for 30 minutes. The crude LPS was washed 3 times with 5 volumes of methanol-acetate, dialysed against 0.01M TRIS-HCL buffer (pH 7.%) with 1% saline and 0.04% sodium azide, digested with lysozyme, RNAse, DNAse (all 25 $\mu$g/ml, 6 hours at room temperature) and proteinase K (50 $\mu$g/ml, another 48 hours incubation at room temperature). The mixture was ultra-centrifuged, then the final LPS pellet was re-suspended in water and lyophilized. Samples of OPS and LPS dissolved in water did not absorb at $A_{260,280}$ and contained less than 1% protein.

For liposomal encapsulation of OPS and LPS, briefly, negatively charged liposomes were prepared using phosphatidylcholine:cholesterol:phosphatidylserine in a molar ration of 7:2:1. The lipids were dissolved in a small volume of chloroform:methanol (2:1 v/v), dried to a thin film on a RotaVap™ (under vacuum, flask was immersed in 37° C. water bath), then further dried in a vacuum chamber to remove residual solvent (Note: the lipids are sensitive to oxygen). Either OPS or LPS in 1% saline (the saline was autoclaved and cooled to remove dissolved oxygen) was added to the lipid film and a thick emulsion was made on the RotaVap™. The emulsion was transferred to centrifuge tubes, purged with nitrogen gas, left for an hour to reconstitute, then re-suspended in 100 mM HEPES buffer (pH 6.7) in normal saline. The liposomes were washed (centrifuged 125,000×g/4° C./30 min., supernatant discarded, pellet re-suspended in HEPES-saline), the preparation was purged with nitrogen gas and the tubes sealed with Parafilm™ until required.

Balb/c mice were 15–16 grams (29–35 days old) females purchased from Charles River (Quebec) and were cared for in accordance with the guidelines set by the Canadian Council for Animal Care. All procedures were reviewed and approved by the Animal Care Committee (members consist of a veterinarian, scientists and lay people) at the Defence Research Establishment Suffield (DRES). Immunization (on weeks 0, 1 and 5) was done by suspending the vaccines in sterile saline and delivering a total of 0.2 ml in 2 subcutaneous and 2 intra-muscular injections. Blood samples were drawn from, and infectious inocula (on week 6) were given by, the intra-venous route using the tail vein which had been mildly warmed under a heat lamp. Spleen counts were assessed by sacrificing each animal (on week 7), aseptically removing the spleen, homogenizing this in 2 aliquots of 1 ml sterile saline, serially diluting the preparation, plating each dilution on Brucella agar (5% $CO_2$, 37° C., 1 week for incubation) and counting the resulting colonies. Protection was identified when the total spleen count was 100-fold (i.e. 2 $\log_{10}$) less than the inoculum given.

Specific IgG and IgM levels against LPS and OPS in serum samples from the weekly bleedings were assayed by an indirect FELISA, as known in the art (Fulton et al., *J. Virol. Methods,* 22, 1988, 149–164). Due to the large number of samples, equal volumes of the sera from the mice (sets of 3–4 mice given the same vaccine concentration) were pooled. Briefly, the wells of the microtitre plates were coated with 50 $\mu$l of *B. abortus* LPS (20 $\mu$g/ml in 0.05M carbonate-bicarbonate buffer, pH 9.6). This antigen was used to detect the antibody response to OPS, liposome encapsulated OPS (LIP-OPS), LPS and liposome encapsulated LPS (LIP-LPS). After blocking steps of 2% bovine serum albumin, 0.1% Tween 20, 0.14% sodium phosphate, 1% NaCl pH 7 (BT-PBS), serially diluted serum samples were added to the wells. The specific IgG and IgM levels were detected by alkaline phosphatase-labelled anti-mouse IgG or IgM conjugates.

Results

1) Mouse Studies at DRES

Balb/c mice were immunized with purified OPS from *Brucella abortus* 1119-3 and initially the results were discouraging. As expected, the IgG or IgM antibody titres (reflective of humoral immunity) were very low with OPS, whether given as a single dose or as multiple (3) doses. The antibody titres were more pronounced when LPS was given as the antigen. The antibody titres could be enhanced when these antigens were liposomal encapsulated, but again the titres were still low for OPS (see FIGS. 1 to 8).

When these mice were challenged with a virulent strain of *B. abortus* 2308, however, OPS did appear to protect the mice from infection. Indeed, the poorer the antibody response to a given antigen, the better appeared to be the protection as shown in Table II which presents date on mice immunized three times with the noted concentration of purified antigens then challenged with *B. abortus* 2308.

Table III compares mice immunized either once or three times with the noted concentrations of purified antigens then challenged with *B. abortus* 30 (another infectious strain that was isolated from an aborted bovine fetus by Agriculture Canada several years ago). Other studies such as those with mice in Chile and with guinea pigs in Colombia appear to suggest that there is a low element of randomness in protection studies, likely due to individual susceptibility or resistance to brucellosis.

2) Guinea Pig Studies (Colombia)

Dr. Olga Marino of the Instituto Colombiano Agropecuario (ICA), Bogota, Colombia, did an independent investigation on the protective properties of the OPS vaccine. Guinea pigs were used as these are perhaps the most sensitive animal species to Brucella infections (Garcia-Carillo, "Laboratory Animal Models for Brucellosis Studies", *Animal Brucellosis* (1990), 423–442, K. Nielsen and J. R. Duncan (ed.)). A vaccine that is protective to these susceptible animals is likely to be protective for humans.

Results for the first set of experiments are not available, although it was reported that 1 mg of OPS was able to protect a 400 g guinea pig from a challenge of $5\times10^4$ cells of *B. abortus* 2308. At the United Nations University Brucellosis Researchers Network meeting in Valdivia, Chile (April, 1995), another study was presented as noted in Table IV. Results were said to be similar to that of before, except that previously 1000 μg was 100% protective while three injections to 1000 μg was only partially effective.

The similarities between the two studies suggest that OPS is protective for guinea pigs against Brucella infection, that single doses are more protective than multiple doses, and that protection appears to be inversely related to antibody production.

3) Swine Study in Venezuela

In Venezuela, swine are infected not with *Brucella abortus* but with *Brucella suis,* a more infectious species of Brucella than the former. The disease is sexually transmitted, passed from an infected boar to a susceptible sow at breeding.

In the presented studies, sows were either left as controls or were vaccinated with different doses of potential vaccines. The swine were cared for six months then both the vaccinates and the controls were mated with the same four infected boars to ensure insemination and infection. The animals were housed in the same general area on a farm and could be identified by ear tags.

Table V gives a brief summary of the results. From the results it was found that:

a) A single dose of 100 μg of OPS (from *B. abortus*) was 100% effective in protecting the sows from *B. suis* infection. Protected swine did not have significant serum titres to Brucella. Not only did the pregnancies come to a successful term, but the litter size averaged 11 to 12 robust piglets. There is good evidence, therefore, that the DRES OPS vaccine, made from *B. abortus* cells, can protect against infections from cross-reactive bacteria (e.g. *B. suis*).

b) For the controls, 68% sero-converted with high titres to Brucella, and of these 45% aborted. For control sows that did come to term, 5% had still-born piglets in their litters. For the remainder, although the litter appeared healthy, the average size was 5 to 6 piglets.

4) Production of 150,000 "Human Eqiuivalent Doses" of Vaccine

If 100 μg of the OPS vaccine can protect a 25 kg sow from a highly virulent strain of *B. suis,* it is likely that 300 μg of the same vaccine will protect a 75 kg person. The initial plan was to produce enough *B. abortus* cells and from this enough OPS vaccine to supply the amounts required for collaborative studies with our allies. However, as DRES has had its Level 3 Contaminant suites under renovations during the term of this task, killed *B. abortus* cells were acquired from external sources. The two sources were:

1) VECOL, Empresa Colombiana de Productos Veterinarios D. C. Calle 26 (Av. El Dorado), No. 82–93 Bogota, Colombia
2) United States Department of Agriculture National Veterinary Services Laboratory 1800 Bayton Road Ames, Iowa, USA, 50010

The OPS vaccine was then extracted from the above cells using the "Rapid Method" reported by Cherwonogrodzky et al. (1990) which was summarized above. It should be noted that Lot #1 differs from Lot #2 in that the former used autoclaving as a source of heat for the hydrolytic release of polysaccharide while the latter used a boiling water bath. For Lot #1, the cells were first washed and re-suspended in 1% NaCl, 2% acetic acid. The cells were then autoclaved but due to a malfunction the conditions were 140° C. instead of 121° C., the pressure was about 23 psi instead of 15 psi, and the time was about 1 hour instead of 30 minutes. Charing and yellowing of the OPS was observed, although the Colombian study with guinea pigs suggests that this did not seriously affect the potency of the vaccine. For the Lot #2 extractions, the cells were washed and re-suspended as before in 1% NaCl, 2% acetic acid, but instead were heated in a boiling water bath at 99° C. for 2 hours. The yield of OPS was less (8 g instead of 30 g per kg) but there was less charing and less yellowing of the vaccine. A total of 45 g (150,000 human equivalent doses) has been purified for research and experimental purposes.

The following is evidence that the *Brucella abortus* OPS vaccine is protective against bacteria other than *B. abortus:*

1) One of the most encouraging results is the absolute protection that the OPS vaccine gave swine against *B. suis* infection. Not only did it offer protection but it is likely that this protection also extends against cross-reactive bacteria as evidenced by the fact that the polysaccharide vaccine used was from *B. abortus* yet protected swine from *B. suis.*

2) The hope was that the vaccine would protect swine from brucellosis. Not only were small amounts (i.e. 100 μg) of vaccine protective, but a single injection protected swine that were exposed to disease six months later. Also, a year after these studies were done, these same swine were protected from any incidence of infection (i.e. the vaccine is long lasting). Curiously, the farm where these swine were kept had an epidemic of *Haemophilis pleuropneumonia.* Unlike the rest of the swine, those immunized with the OPS vaccine remained healthy. Recently, similar studies were done in Venezuela except that the vaccine was given orally to swine rather than by injection. The same concentration of vaccine (except given orally) gave the same effective level of protection against brucellosis. Oral vaccination raises the possibility that food pellets with vaccine may be able to vaccinate wildlife. 3) Related work at DRES has found that the OPS vaccine may be a powerful immuno-modulator, enhancing general immunity against disease. In this work it was found that the OPS from *Yersinia enterocolitica* 0:9 can be used to replace the OPS from *B. abortis.* This is the first evidence that the OPS vaccine made from any of the cross-reactive bacteria, such as those in Table I, may be of complete or partial protection against the other noted bacteria.

As mentioned above, FIGS. 1 to 8 give a representation of the humoral response of the immunized mice to different potential vaccines of different concentrations. General trends in these responses are summarized below:

a) OPS appeared to be a poor immunogen. Anti-Brucella IgG and IgM levels after a single dose were either undetectable or at the lower limits of detection, even when OPS was liposome encapsulated. When multiple injections of OPS were given, anti-Brucella IgM levels were still at the lower limit of detection and then only detectable for the higher concentrations of OPS given. Anti-Brucella IgG levels were higher for multiple injections than for a single dose of OPS, but even then the response was at the limit of detection for the low concentrations of OPS given. Liposomal encapsulation of OPS did enhance anti-Brucella IgG titres about 4 fold.

b) LPS appeared to be a better immunogen than OPS. The anti-Brucella IgG and IgM levels were higher with greater concentrations of antigens given, were higher for multiple rather than single dose injections, and were higher when the LPS was liposomal encapsulated. For a single dose of 0.1 or 1 μg LPS or LIP-LPS, no anti-Brucella IgG levels were detected. Either the levels were below the limits of detection or the concentrations were below a required threshold for an IgG response.

c) Despite the above trends, when the same mice were challenged with *B. abortzis* (similar results were observed for strains 30 and 2308 and hence have been combined), protection did not appear to be correlated with anti-Brucella IgG or IgM levels (see Table VI). Indeed, the results suggest an inverse relationship whereby the best protection was observed for mice injected with antigens that gave the lowest anti-Brucella antibody titres (i.e. single doses, OPS).

Discussion

In the presented study, it has been found that purified OPS is a poor immunogen for anti-Brucella IgG or IgM titres in the mouse. These titres can be enhanced if multiple rather than a single dose is given, if OPS is associated with lipids (either in the LPS form or liposomal encapsulated) and if high concentrations are used. It was also observed that these titres had little to do with protection, and indeed there appeared to be a general trend that greater protection was correlated with poorer anti-Brucella responses. This lack of correlation is understandable given that the Brucella species are facultative parasitic bacteria that can invade white blood cells, organs and bone marrow (F. M. Enright, *Animal Brucellosis* (1990), 301–320, K. Nielsen and J. R. Duncan (ed.); P. Nicoletti and A. J. Winter, ibid, 88–95), sequestering themselves away from the bactericidal effects of antibodies. Although antibodies are unlikely to have an influence on established intra-cellular infections, these still have a significant effect on reducing bacterial counts circulating in the blood after an initial inoculation or in humoral bacteraemia (L. B. Corbeil et al., *Infect. Immun. (*1988) 3251–3261).

As cattle immunized with *B. abortus* S19 are resistant to brucellosis, it is likely that some antigens can induce a cell-mediated immunity (Nicoletti and Winter, 1990). The present study indicates that purified OPS can induce such an immunity and this has subsequently been supported in other studies using mice.

As the OPS of *B. abortus* was an effective vaccine against brucellosis, other sources for this component may also be possible. Possibilities are *Escherichia coli* recombinants, OG6 and OG8, carrying Brucella genes, cross-reactive bacteria such as *Yersinia enterocolitica* O:9 and *Escherichia hermannii,* and defective strains of Brucella. For the latter, colonies of *B. melitensis* B 115 are rough in appearance because, even though they do produce OPS (R. Diaz et al., *J. Clin. Microbiol.* (1979), 10, 37–41), this strain is defective on combining it to its LPS and hence either store or secrete the OPS. Similar defective strains may not only be a source of OPS in vitro, but may be a potential vaccine candidate as a result of their secretion of the OPS in vivo.

Conclusions

As the O-polysaccharide, or OPS, is an integral part of the smooth-lipopolysaccharide, or LPS, an immunosorbant assay (the indirect FELISA) was used to quantify antibodies in mice immunized with either *B. abortus* OPS or LPS. The present results confirmed the view that LPS was more immunogenic than OPS, that multiple injections gave better response than a single injection, and that liposome encapsulation of antigens raised anti-Brucella IgG or IgM titres. The humoral response appeared to have little correlation with protection against brucellosis, and indeed the most effective vaccine appeared to have been purified OPS, and even then one injection of this novel vaccine appeared to have been more effective than multiple injections.

This suggests that recombinants capable of expressing OPS, cross-reactive bacteria that express similar polysaccharides, or defective strains of Brucella that synthesize but do not couple the OPS to LPS, may be novel vaccine candidates.

It has been found in other studies that Brucella vaccines or filtrates of Brucella cultures gave therapeutic relief for brucellosis patients. In view of this finding and the results presented above it can be concluded that the OPS vaccine of the present invention can be used as a treatment after infection.

Although the invention has been described with reference to certain specific embodiments, various modifications thereof will be apparent to those skilled in the art without departing from the spirit and scope of the invention as outlined in the appended claims.

TABLE I

OPS of Cross-Reactive Bacteria

| Bacterium | O-Polysaccharide on their PLS[a] |
|---|---|
| *Brucella abortus* | (1,2-linked) perosamine |
| *Yersinia enterocolitica* O:9 | (1,2-linked) perosamine |
| *Brucella melitensis* | (1,3-linked) perosamine |
| *Escherichia hermanii* | (1,3-linked) perosamine |
| *Brucella suis* | (1,2/1,3-linked) perosamine |
| *Vibrio cholerae* | glycero-tetronic perosamine |
| *Salmonella landau* | glu,fu,acetyl-gal,acetyl-perosamine |
| *Salmonella godesburg* | glu,fu,acetyl-gal,acetyl-perosamine |
| *Escherichia coli* O157:H7 | glu,fu,acetyl-gal,acetyl-perosamine |
| *Pseudomonas maltophilia* 555 | rham,acetyl-gal,acetyl-perosamine |
| *Francisella tularensis* | dideoxy sugar-perosamine |
| *Yersinia pestis* | ?-perosamine[b] |

[a]perosamine, 4-formamido-4,6-dideoxy-D-mannose; glu, D-glucose; fu, L-fructose; gal, D-galactose; rham, D-rhamnose
[b]some strains of plague cross-react with Brucella, the mechanism is unknown (personal communication, Dr. M Corbel, 1994)

TABLE II

Balb/c Mice Vaccinated and then Challenged with *B. abortus* 2308

| | | Antibody titre[1] | | Spleen Count | Protection | |
|---|---|---|---|---|---|---|
| Antigen | | IGg | IgM | (log$_{10}$CFU)[2] | (no./total) | % |
| None | | <6.6 | <6.6 | 6.1, 6.5, 6.5, 6.6 (avg. 6.4) | 0/4 | 0 |
| LPS | 1 µg | 8.6 | 7.6 | 3.7, 4.8, 4.8, 5.8 | 1/4 | 25 |
| | 100 µg | 11.6 | 8.6 | 2.6, 2.6, 3.7, 6.0 | 3/4 | 75 |
| LIP-LPS | 1 µg | 11.6 | 7.6 | 3.0, 3.2, 4.6, 5.9 | 2/4 | 50 |
| | 100 µg | 13.6 | 10.6 | 4.3, 4.7, 4.7, 6.3 | 1/4 | 25 |
| OPS | 1 µg | 7.6 | <6.6 | 3.7, 5.0, 5.5, 5.6 | 1/4 | 25 |
| | 100 µg | 8.6 | 6.6 | 0, 0, 3.2, 3.4 | 4/4 | 100 |
| LIP-OPS | 1 µg | 7.6 | <6.6 | 0, 0, 3.3, 3.8 | 4/4 | 100 |
| | 100 µg | 11.6 | 7.6 | 3.3, 3.4, 3.7, 4.5 | 3/4 | 75 |

[1]Log$_2$ of average reciprocal antibody titres at 6 weeks of immunization.
[2]Initial inoculum was $5 \times 10^4$ or 4.7 log$_{10}$ CFU. Each number is the spleen count for a single mouse.

TABLE III

Single vs. Multiple Injections of Antigens as Vaccines in the Protection of Balb/c Mice Against *B. abortus* 30

| Antigen | | Single Injection of Antigen: Spleen Counts ($log_{10}$ CFU) | Single Injection of Antigen: Protection (no./total) (%) | Multiple Injections of Antigens: Spleen Counts ($log_{10}$ CFU) | Multiple Injections of Antigens: Protection (no./total) (%) |
|---|---|---|---|---|---|
| Control (none) | | 4.78, 5.20, 5.69, 4.59, 4.00 | 0/5 (0%) | see previous column | see previous column |
| LPS | 100 μg | 3.48, 0, 3.48, | 1/3 (33%) | 0, 5.20 | 1/2 (50%) |
| | 10 μg | 3.84, 4.30, 0 | 1/3 (33%) | 4.81, 3.60, 3.30 | 0.3 (0%) |
| | 1 μg | 0, 0, 8.0 | 2/3 (66%) | 0, 4.61 | 1/2 (50%) |
| | 0.1 μg | 4.15, 5.08, 5.78 | | 0, 5.34 | 1/2 (50%) |
| LIP-LPS | 100 μg | 0, 0 | 2/2 (100%) | 0, 0, 4.82 | 2/3 (66%) |
| | 10 μg | 0, 3.60, 0 | 2/3 (66%) | 0, 0, 0 | 3/3 (100%) |
| | 1 μg | 0, 5.11 | 1/2 (50%) | 0, 5.36 | 1/2 (50%) |
| | 0.1 μg | 0, 5.25, 3.0 | 1/3 (33%) | 0, 0 | 2/2 (100%) |
| OPS | 100 μg | 0, 0, 0 | 3/3 (100%) | 0, 4.40 | 1/2 (50%) |
| | 10 μg | 0, 0 | 2/2 (100%) | 3.60, 3.30, 0 | 1/3 (33%) |
| | 1 μg | 0, 0 | 2/2 (100%) | 0, 0 | 2/2 (100%) |
| | 0.1 μg | 0, 0, 0 | 3/3 (100%) | 3.00, 5.23 | 0.2 (0%) |
| LIP-OPS | 100 μg | 8.18, 0 | 1/2 (50%) | 0, 0, 0 | 3/3 (100%) |
| | 10 μg | 3.84, 4.20, 0 | 1/3 (33%) | 0, 0, 0 | 3/3 (100%) |
| | 1 μg | 3.85, 3.48, 0 | 1/3 (33%) | 5.62, 5.11, 4.28 | 0.3 (0%) |
| | 0.1 μg | 0, 0 | 2/2 (100%) | 0, 0, 5.04 | 2/3 (66%) |

Mice were immunized on week 1 for single injection, weeks 1, 2 and 5 (intramuscular) for multiple injections. On week 7 mice were challenged with $5\times10^4$ ($log_{10}$ of 4.70) of *B. abortus* 30, on week 8 the mice were sacrificed and their spleens assayed for bacteria.

TABLE IV

Guinea Pigs Immunized with OPS and Challenged with *B. abortus* 2308

| Antigen | | Infected Animals/Total | % Protection |
|---|---|---|---|
| None (controls) | | 6/6 | 0% |
| Single dose of OPS | 10 μg | 1/4 | 75% |
| | 100 μg | 1/4 | 75% |
| | 1000 μg | 3/4 | 25% |
| Three doses of OPS | 3 × 10 μg | 3/4 | 25% |
| | 3 × 100 μg | 3/4 | 25% |
| | 3 × 1000 μg | 0/4 | 100% |

TABLE V

Venezuelan Swine Study for Vaccinated and Control Sows Challenged with *Brucella suis*

| No. | Vaccine | Amount | Dose | Result | 1 year later |
|---|---|---|---|---|---|
| 10 | Bab-OPS | 100 μg | 1 | no abort., sero− | protected |
| 10 | Bab-OPS | 500 μg | 1 | no abort., sero+/− | protected |
| 10 | Bab-OPS | 100 μg | 3 | no abort., sero− | protected |
| 10 | Bab-OPS | 500 μg | 3 | no abort., sero+/− | protected |
| 10 | Bsu-OPS | 100 μg | 1 | no abort., sero− | protected |
| 10 | Bsu-OPS | 500 μg | 1 | no abort., sero+/− | protected |
| 10 | Bsu-OPS | 100 μg | 3 | no abort., sero+/− | protected |
| 10 | Bsu-OPS | 500 μg | 3 | no abort., sero+/− | protected |
| 10 | Bsu-cell | 100 μg | 1 | no abort., sero+ | protected |
| 10 | Bsu-cell | 500 μg | 1 | no abort., sero+ | protected |

TABLE V-continued

Venezuelan Swine Study for Vaccinated and Control Sows Challenged with *Brucella suis*

| No. | Vaccine | Amount | Dose | Result | 1 year later |
|---|---|---|---|---|---|
| 10 | Bsu-cell | 100 μg | 3 | no abort., sero+ | protected |
| 10 | Bsu-cell | 500 μg | 3 | no abort., sero+/+ | protected |
| 10 | RB51 | $10^6$ | 1 | no abort., sero− | protected |
| 10 | RB51 | $10^7$ | 1 | no abort., sero− | protected |
| 10 | RB51 | $10^8$ | 1 | no abort., sero− | protected |
| 10 | RB51 | $10^9$ | 1 | no abort., sero− | protected |
| 30 | Controls | | | 31% abort., 68% sero+ | 25% abortions |

Bab-OPS is *Brucella abortus* 11 19-3 O-polysaccharide vaccine, Bsu-OPS is an O-polysaccharide vaccine produced in Venzuela from *B. suis,* Bsu-cell is *B. suis* cells killed with 2% phenol, RB51 is an attenuated live vaccine strain of *B. abortus* from Dr. G. Shurig, Blacksburg, W.V.

TABLE VI

Protection Against *Brucella abortus* for Balb/c Mice Given Different Antigen Vaccines

| Injection[a] | Vaccine[b] | | Spleen Count[c] | Protection[d] | Uninfected Mice[e] |
|---|---|---|---|---|---|
| | None (control) | | 5.48 ± 0.24 | 0.12 (0%) | 0/12 (0%) |
| Single Dose (wk 0) | OPS: | 1 μg | 1.53 ± 0.69 | 6/6 (100%) | 3/6 (50%) |
| | | 100 μg | 2.24 ± 0.85 | 4/7 (57) | 3/7 (43%) |
| | LIP-OPS: | 1 μg | 3.26 ± 0.55 | 1/7 (14%) | 1/7 (14%) |
| | | 100 μg | 4.17 ± 1.06 | 1/7 (14%) | 1/7 (14%) |
| | LPS: | 1 μg | 4.01 ± 1.12 | 2/7 (29%) | 2/7 (29%) |
| | | 100 μg | 3.54 ± 0.70 | 1/7 (14%) | 1/7 (14%) |
| | LIP-LPS: | 1 μg | 3.12 ± 0.71 | 3/7 (42%) | 1/7 (14%) |
| | | 100 μg | 1.43 ± 0.64 | 6/6 (100%) | 3/6 (50%) |
| Multiple Doses (wks 0, 1, 5) | OPS: | 1 μg | 3.85 ± 0.66 | 2/10 (20%) | 2/10 (20%) |
| | | 100 μg | 3.07 ± 0.70 | 3/10 (30%) | 3/10 (30%) |
| | LIP-OPS: | 1 μg | 3.38 ± 0.55 | 3/11 (27%) | 2/11 (18%) |
| | | 100 μg | 2.56 ± 0.51 | 3/11 (27%) | 3/11 (27%) |
| | LPS: | 1 μg | 3.39 ± 0.54 | 5/10 (50%) | 1/10 (10%) |
| | | 100 μg | 2.88 ± 0.60 | 5/10 (50%) | 2/10 (20%) |
| | LIP-LPS: | 1 μg | 3.38 ± 0.52 | 6/10 (60%) | 1/10 (10%) |
| | | 100 μg | 3.46 ± 0.61 | 5/11 (45%) | 2/11 (18%) |

[a]dose given in 2 subcutaneous and 2 intra-muscular injections.
[b]total amount for each dose.
[c]average (with standard error about the mean) *B. abortus* counts ($\log_{10}$ colony forming units) for spleens.
[d]number of mice with 2 $\log_{10}$ less *B. abortus* c.f.u. in spleens/total group number.
[e]number of mice with no detectable *B. abortus* in spleens/total group number.

The Embodiments of the invention in which an Exclusive Property or privilege is claimed are defined as follows:

1. A method of stimulating cell-mediated immunity against brucellosis in a mammal consisting of administering to the mammal a composition consisting of outer-polysaccharide extracted from Brucella or any bacteria cross reactive thereto, wherein said administration of said composition stimulates cell-mediated immunity of said mammal.

2. The method of claim 1, wherein outer-polysaccharide is administered intramuscularly, subcutaneously, intraperitoneally or orally.

3. A method of enhancing cell-mediated immunity against bacterial infection from *Brucella abortus, Brucella melitensis, Francisella tularensis, Vibrio cholerae. Pseudomonas maltophila* 555, *Escherichia coli O*:157, H:7, *Escherichia hermannii, Yersinia enterocolitica O*:9, *Salmonella landau or Salmonella godesberg* in a mammal consisting of administering to said mammal a composition consisting of outer-polysaccharide extracted from any one of said bacteria, wherein said administration of said composition enhances cell-mediated immunity of said mammal.

4. The method of claim 3, wherein outer-polysaccharide is administered intramuscularly, subcutaneously, intraperitoneally or orally.

5. A method of claim 1, wherein the Brucella is *Brucella abortus.*

6. A method of protecting a mammal against brucellosis consisting of administering to said mammal a composition consisting of outer-polysaccharide extracted from Brucella or any bacteria cross reactive thereto to increase cell-mediated immunity of said mammal.

7. A method of claim 6, wherein said Brucella is *Brucella abortus.*

8. A method of claim 6, wherein said outer polysaccharide is administered intramuscularly, subcutaneously, intraperitoneally or orally.

9. A method of protecting a mammal against bacterial infection from *Brucella abortus, Brucella melitensis, Francisella tularensis, Vibrio cholerae. Pseudomonas maltophila* 555, *escherichia coli O*:157, *H*:7, *Escherichia hermannii, Yersinia enterocolitica O*:9, *Salmonella landau or Salmonella godesberg* consisting of administering to said mammal a composition consisting of outer-polysaccharide extracted from any one of said bacteria to increase cell-mediated immunity of said mammal.

10. A method of claim 9, wherein said outer polysaccharide is administered intramuscularly, subcutaneously, intraperitoneally or orally.

11. A method of protecting a mammal against brucellosis consisting of administering to said mammal a composition consisting of outer-polysaccharide extracted from Brucella or any bacteria cross reactive to enhance cell-mediated immunity of said mammal.

12. A method of claim 11, wherein said Brucella is *Brucella abortus.*

13. A method of claim 11, wherein said outer polysaccharide is administered intramuscularly, subcutaneously, intraperitoneally or orally.

* * * * *

UNITED STATES PATENT AND TRADEMARK OFFICE

CERTIFICATE OF CORRECTION

PATENT NO. : 5,951,987
DATED : September 14, 1999
INVENTOR(S) : Cherwonogrodzky et al.

It is certified that error appears in the above-identified patent and that said Letters Patent is hereby corrected as shown below:

Title page,
Related U.S. Application Data:
Insert -- [60] Provisional Application No. 60/ 002,623, filed 22 August 1995. --

Column 1,
Line 3, after the Title, insert: -- This application claims priority under 35 USC 119 to foreign application number 2,164,155 Canada filed 30 November 1995 and provisional application 60/002,623 filed 22 August 1995. --.

Figure 1A:
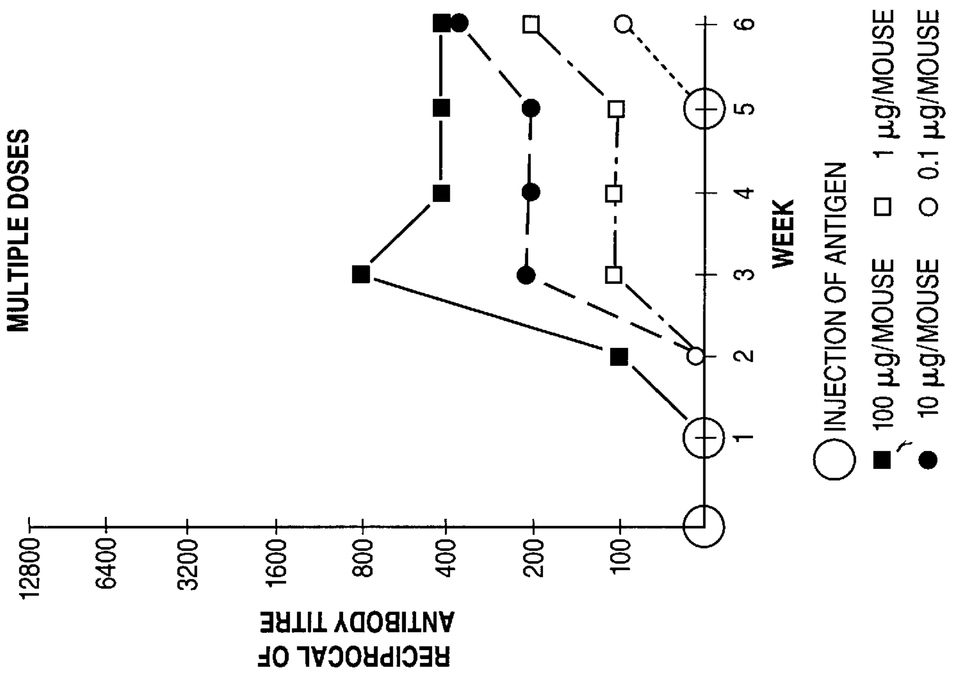

Column 2,
Lines 10-11, delete "FIGS. 1 to 8… tests." and insert,

-- Figures 1A (multiple doses) and 1B (single dose) show titres of IgG for Balb/c mice given *Brucella abortus* OPS.

Figure 2B:
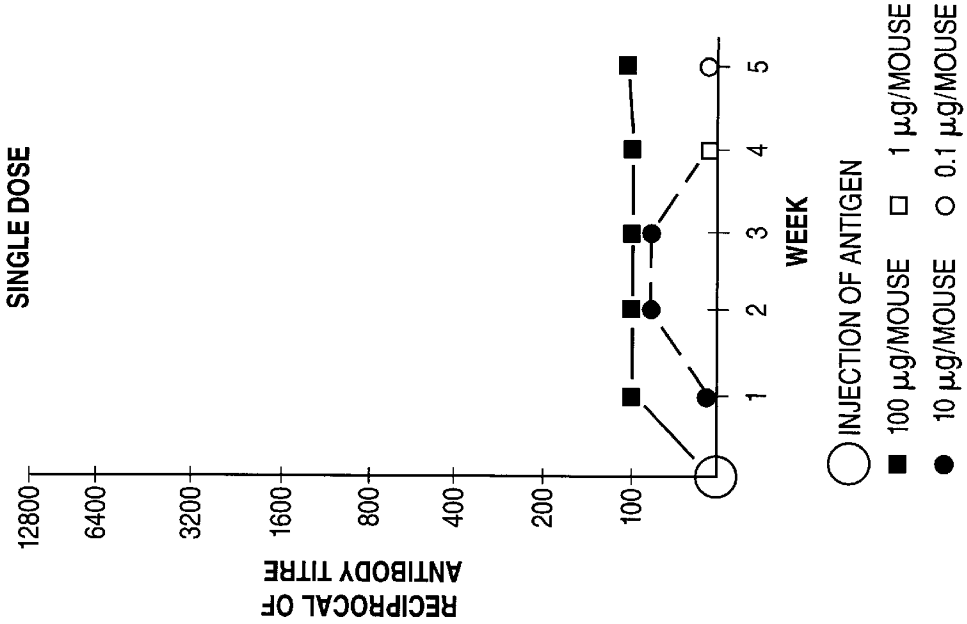
Figure 2A:
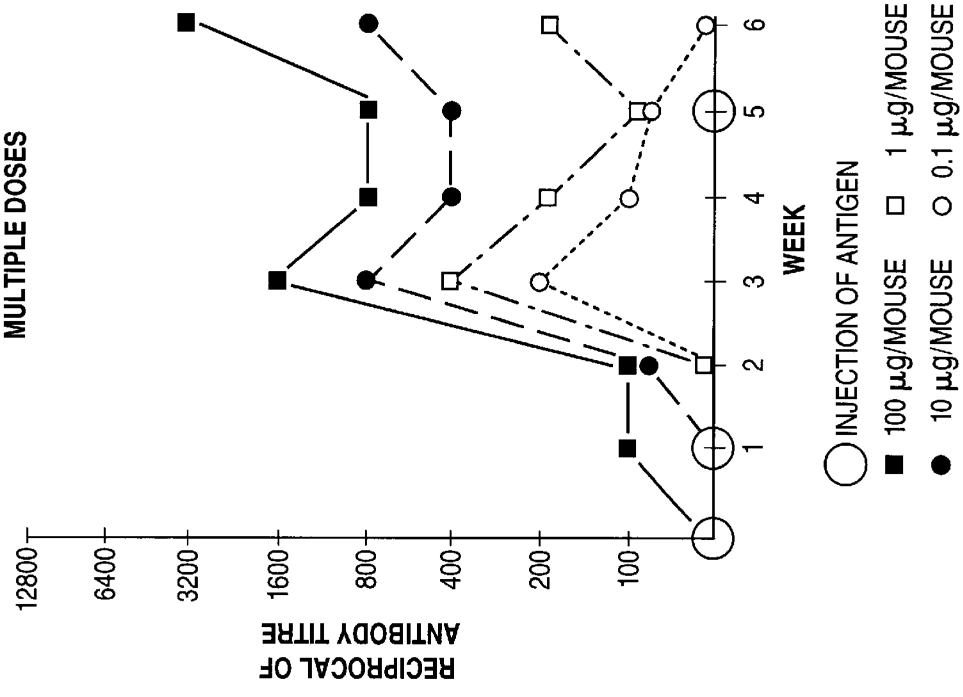

Figures 2A (multiple doses) and 2B (single dose) show titres of IgG for Balb/c mice given *Brucella abortus* LIP-OPS.

Figure 3B:
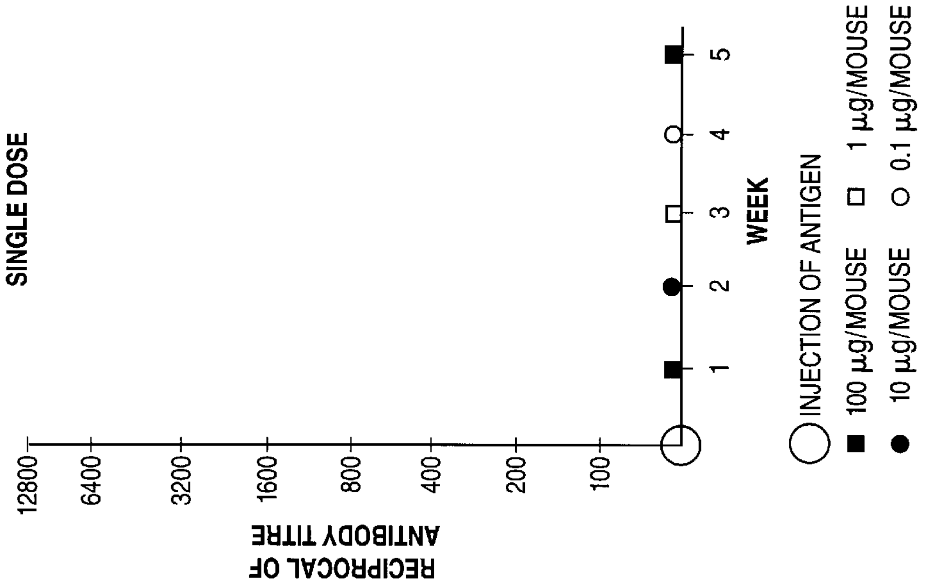
Figure 3A:
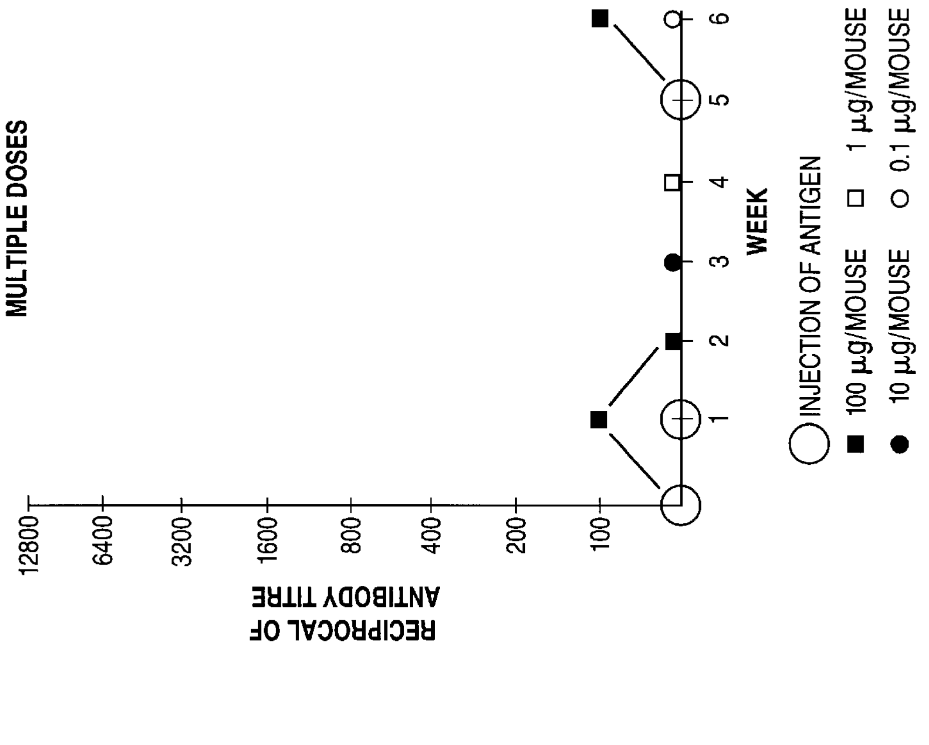

Figures 3A (multiple doses) and 3B (single dose) show titres of IgM for Balb/c mice given *Brucella abortus* OPS.

Figure 4A:
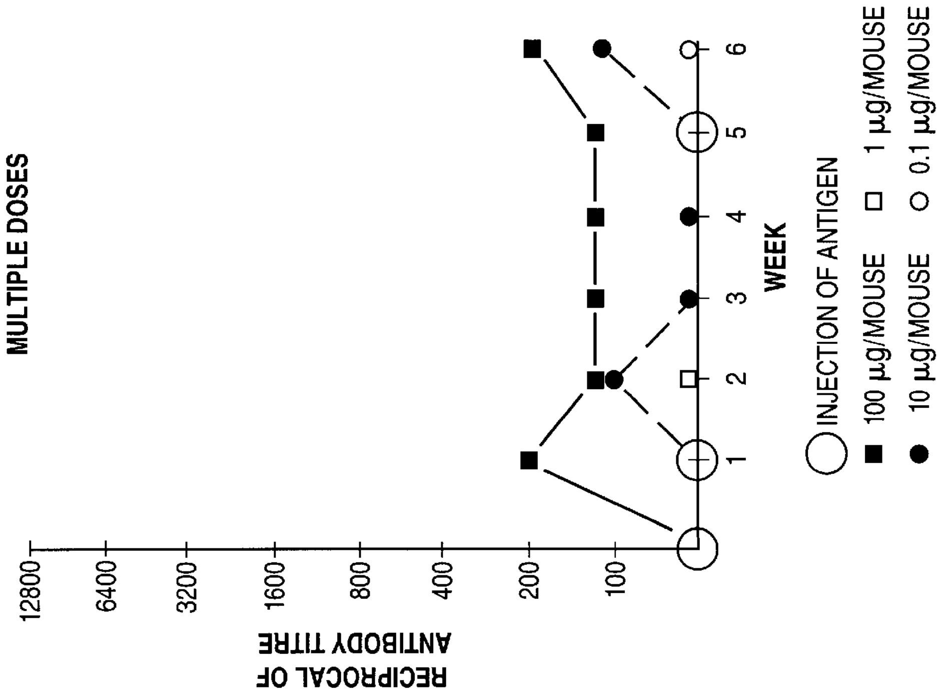
Figure 4B:
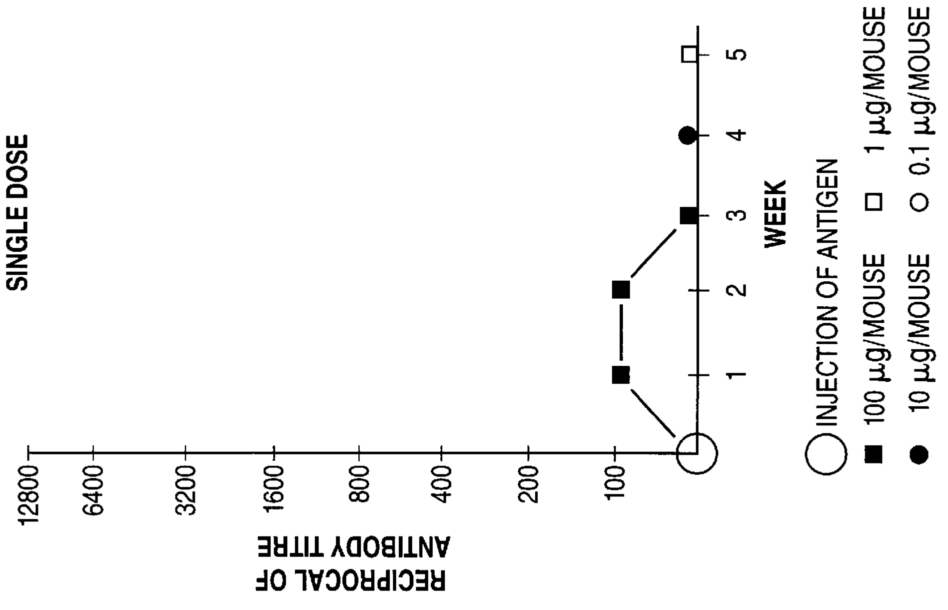

Figures 4A (multiple doses) and 4B (single dose) show titres of IgM for Balb/c mice given *Brucella abortus* LIP-OPS.

Figure 5B:
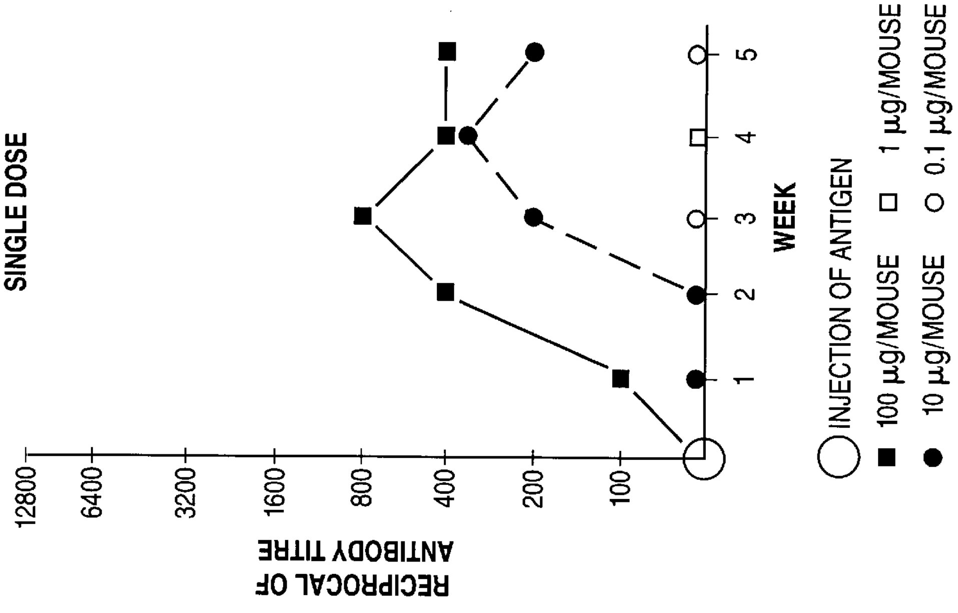
Figure 5A:
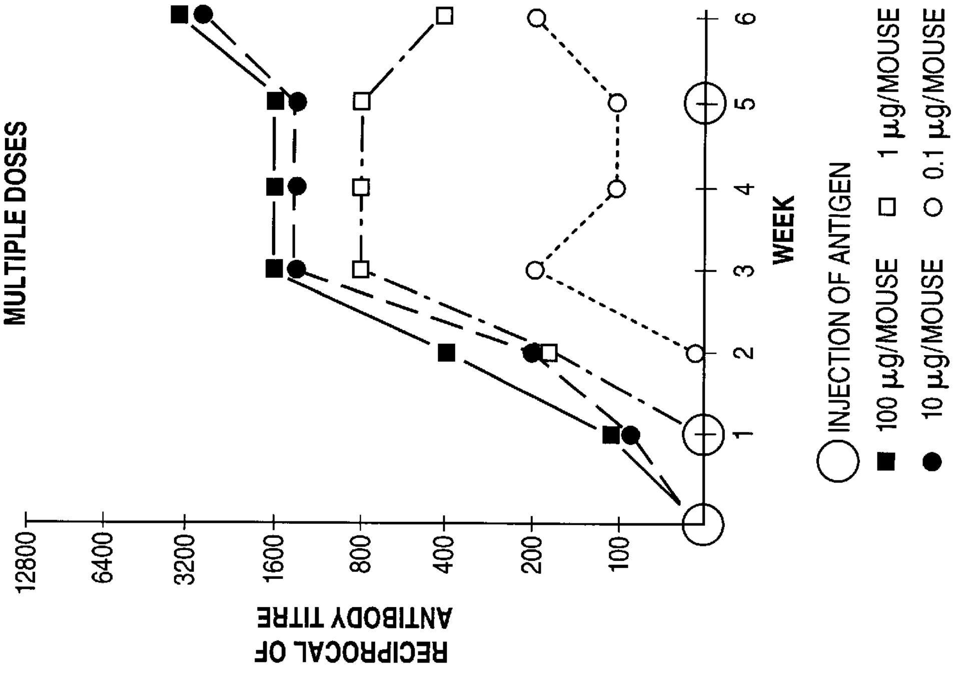

Figures 5A (multiple doses) and 5B (single dose) show titres of IgG for Balb/c mice given *Brucella abortus* LPS.

Figure 6A:
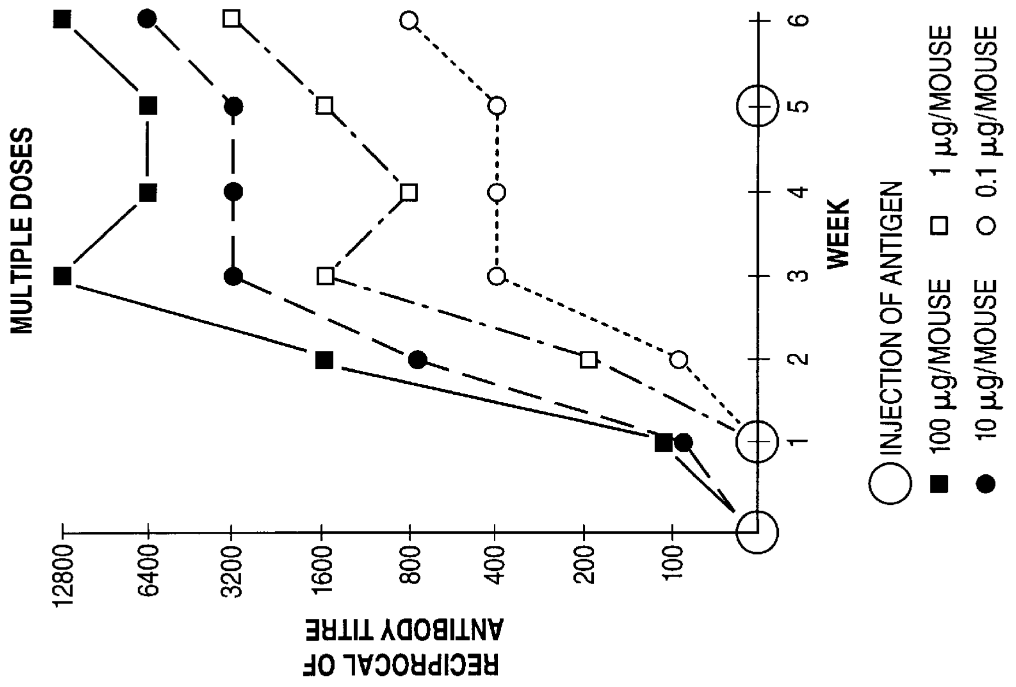
Figure 6B:
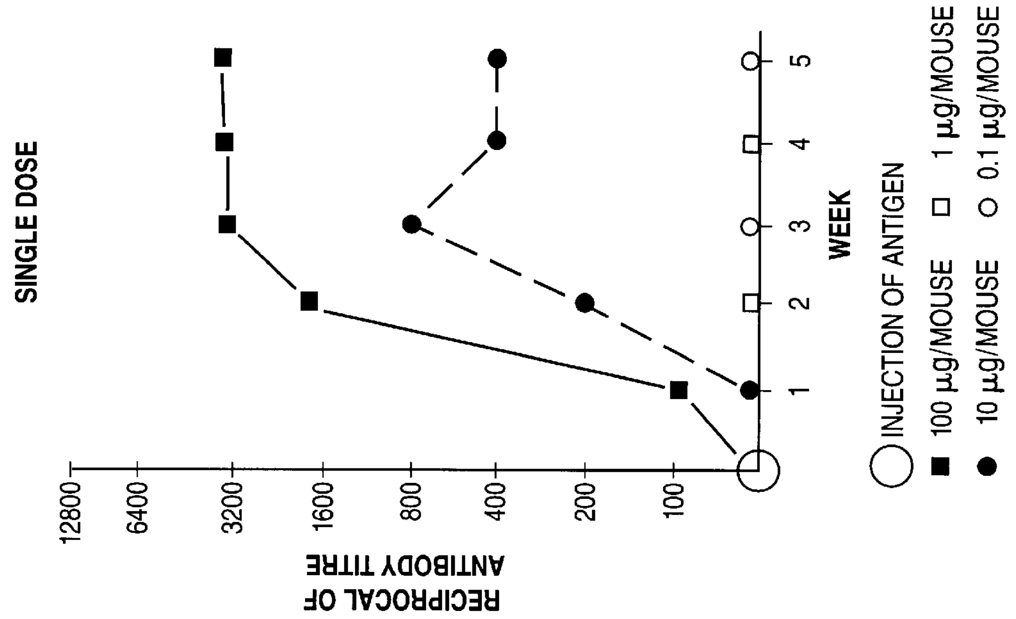

Figures 6A (multiple doses) and 6B (single dose) show titres of IgG for Balb/c mice given *Brucella abortus* LIP-LPS.

UNITED STATES PATENT AND TRADEMARK OFFICE
CERTIFICATE OF CORRECTION

PATENT NO. : 5,951,987
DATED : September 14, 1999
INVENTOR(S) : Cherwonogrodzky et al.

Figure 7B:
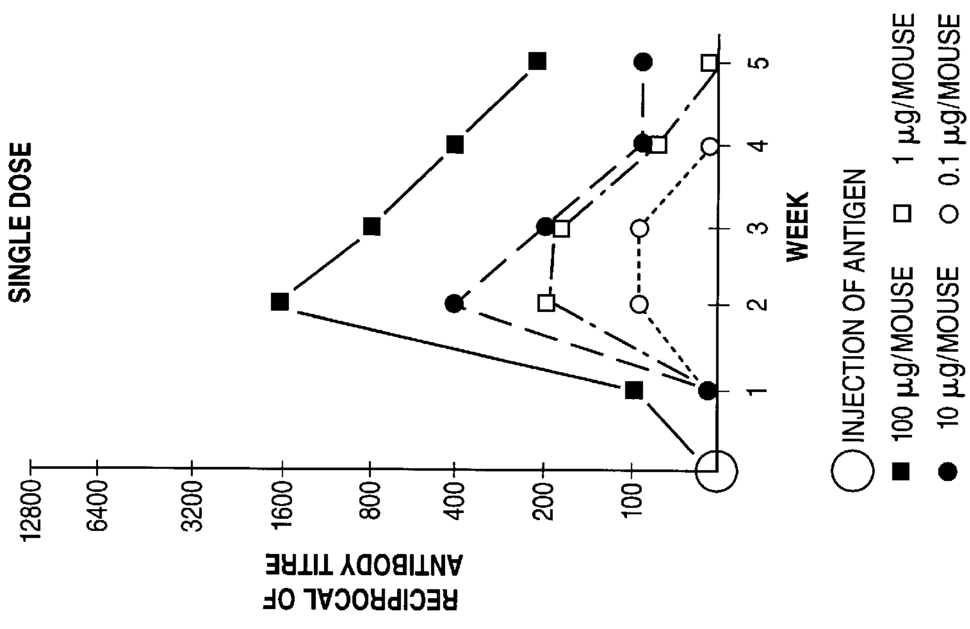
Figure 7A:
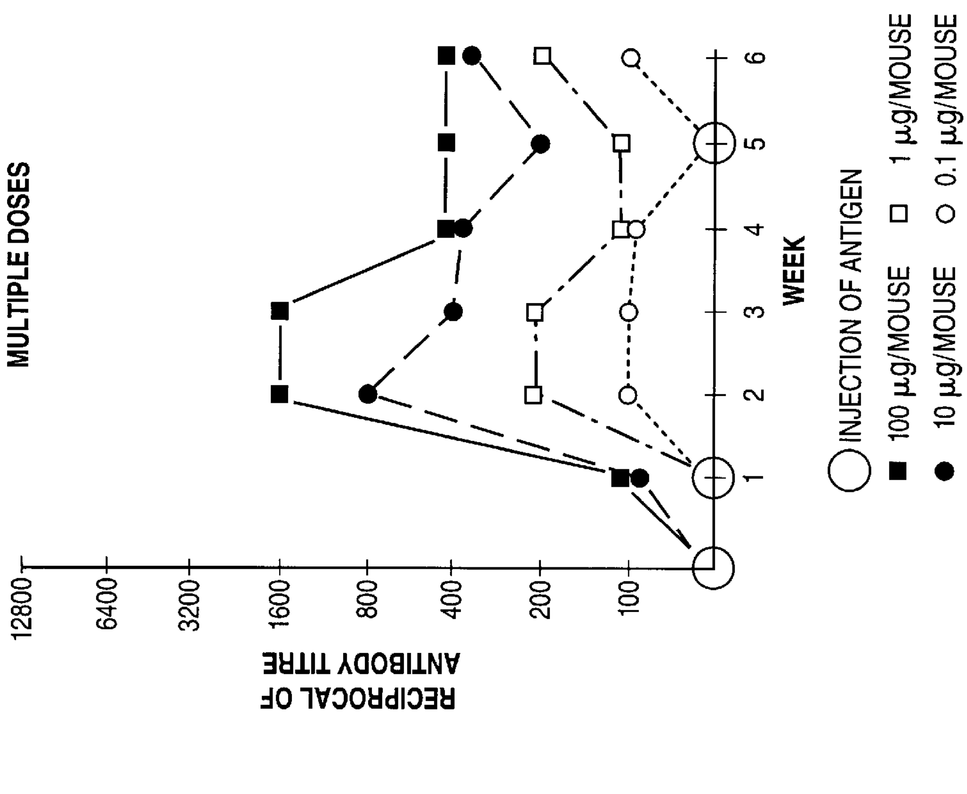

It is certified that error appears in the above-identified patent and that said Letters Patent is hereby corrected as shown below:

Column 2, lines 10-11 cont'd,
Figures 7A (multiple doses) and 7B (single dose) show titres IgM for Balb/c mice given *Brucella abortus* LPS.

Figure 8A:
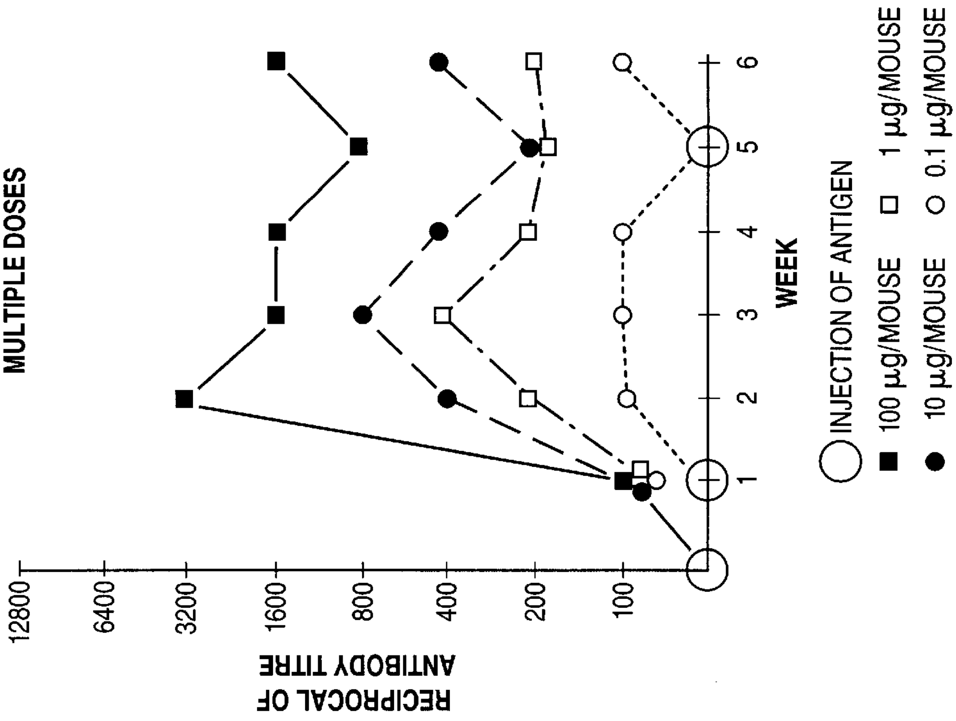
Figure 8B:
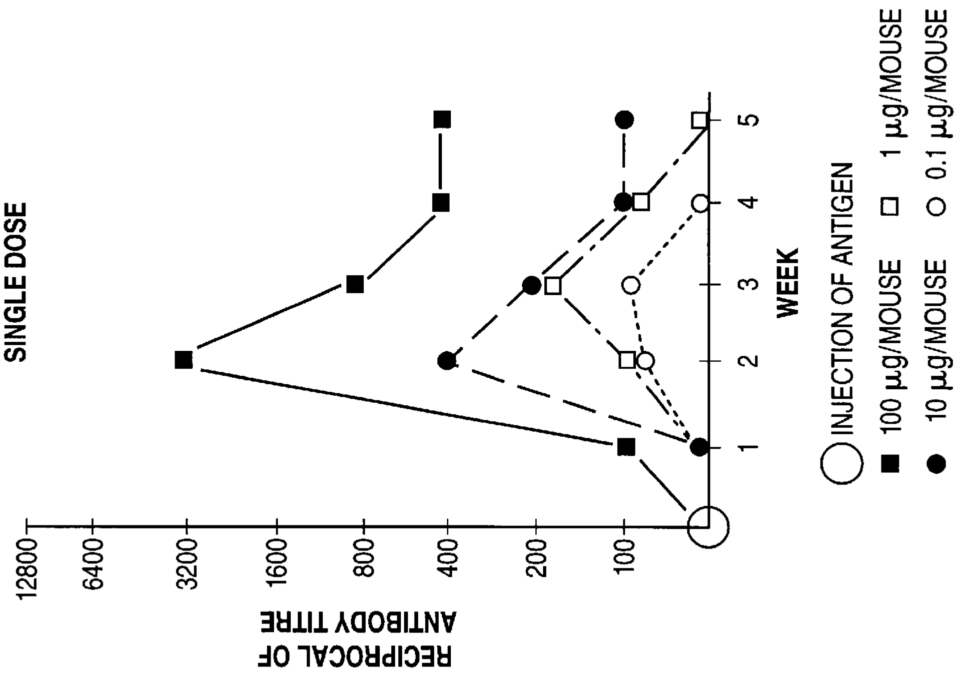

Figures 8A (multiple doses) and 8B (single dose) show titres IgM for Balb/c mice given *Brucella abortus* LIP-LPS. --

Signed and Sealed this

Sixth Day of August, 2002

*Attest:*

JAMES E. ROGAN

*Attesting Officer* *Director of the United States Patent and Trademark Office*